United States Patent [19]
Douglas et al.

[11] Patent Number: 5,872,713
[45] Date of Patent: Feb. 16, 1999

[54] SYNCHRONIZED ANALYTE TESTING SYSTEM

[75] Inventors: Joel S. Douglas, Santa Clara; Karen R. Drexler, Los Altos Hills; Jeffrey N. Roe, San Ramon, all of Calif.

[73] Assignee: Mercury Diagnostics, Inc., Scotts Valley, Calif.

[21] Appl. No.: 960,866

[22] Filed: Oct. 30, 1997

Related U.S. Application Data

[60] Provisional application No. 60/029,201 Oct. 30, 1996.
[51] Int. Cl.$^6$ ...................................................... G06F 15/00
[52] U.S. Cl. ............................ 364/413.09; 435/4; 435/14; 435/808; 435/817; 422/56; 422/58; 422/61; 422/67; 422/82.01; 422/82.06; 204/403; 204/406; 204/407
[58] Field of Search .................................. 435/4, 14, 808, 435/817; 436/164, 169; 422/56, 58, 61, 67, 82.01, 82.02, 82.05, 82.06; 364/413.09; 204/403, 406, 407

[56] References Cited

U.S. PATENT DOCUMENTS

| | | |
|---|---|---|
| D. 323,893 | 2/1992 | Arioka . |
| D. 332,833 | 1/1993 | Lauks et al. . |
| D. 351,469 | 10/1994 | Okamoto et al. . |
| D. 371,198 | 6/1996 | Savage et al. . |
| D. 371,605 | 7/1996 | Wong et al. . |
| D. 378,612 | 3/1997 | Clark et al. . |
| 3,298,789 | 1/1967 | Mast . |
| 3,960,497 | 6/1976 | Acord . |
| 3,992,158 | 11/1976 | Przybylowicz et al. . |
| 4,042,335 | 8/1977 | Clement . |
| 4,140,963 | 2/1979 | Rao et al. . |
| 4,144,306 | 3/1979 | Figueras . |
| 4,195,641 | 4/1980 | Joines et al. . |
| 4,199,261 | 4/1980 | Tidd et al. . |
| 4,258,001 | 3/1981 | Pierce et al. . |

(List continued on next page.)

FOREIGN PATENT DOCUMENTS

| | | |
|---|---|---|
| 0110173 | 6/1984 | European Pat. Off. . |
| 0351891 | 8/1984 | European Pat. Off. . |
| 0140337 | 5/1985 | European Pat. Off. . |
| 0453283 | 10/1991 | European Pat. Off. . |
| 0638805 | 2/1995 | European Pat. Off. . |
| 0656423 | 6/1995 | European Pat. Off. . |
| 0735369 | 10/1996 | European Pat. Off. . |
| 0759555 | 2/1997 | European Pat. Off. . |
| 0769558 | 4/1997 | European Pat. Off. . |
| 0799896 | 10/1997 | European Pat. Off. . |
| 2090659 | 7/1982 | United Kingdom . |
| WO 8501747 | 4/1985 | WIPO . |
| WO 9118548 | 12/1991 | WIPO . |
| WO 9613707 | 5/1996 | WIPO . |

OTHER PUBLICATIONS

Arnold, et al., "Determination of Physiological . . . ," Anal Chem, Jul. 15, 1990, 62, pp. 1457–1464.
Ash, et al., "A Subcutaneous Capillary Filtrate . . . ," ASAIO Journal, 1993, pp. M699–M705.
Dupuy, et al., "Quantitative Analysis of Aqueous . . . ," SPIE, vol. 1575, 1991, pp. 501–502.
Ginsberg., "An Overview of Minimally . . . ," Clinical Chem, v 38, 1992, pp. 1596–1600.
Mendelson, et al., "Blood Glucose Measurement by Multiple . . . ," IEEE, 1990, pp. 458–465.
Turner, et al., "Diabetes Mllitus: Biosensors for . . . ," Biosensors, 1985, pp. 85–115.

*Primary Examiner*—Jeffrey Stucker
*Attorney, Agent, or Firm*—Burns, Doane, Swecker & Mathis, LLP

[57] ABSTRACT

An analyte detection system is provided with calibration information uniquely specific to the set of test strips to which the sample is to be applied. The calibration information may be stored in permanent memory of the testing device, such that the device is discarded after use of all the test strips in a kit, or it may be stored in a calibration chip accompanying the set of test strips and distributed therewith, thereby enabling re-use of the testing device with a different set of test strips and associated calibration chip.

39 Claims, 6 Drawing Sheets

U.S. PATENT DOCUMENTS

| | | |
|---|---|---|
| 4,420,564 | 12/1983 | Tsuji et al. . |
| 4,622,974 | 11/1986 | Coleman et al. . |
| 4,627,445 | 12/1986 | Garcia et al. . |
| 4,637,403 | 1/1987 | Garcia et al. . |
| 4,637,978 | 1/1987 | Dappen . |
| 4,703,756 | 11/1987 | Gough et al. . |
| 4,704,029 | 11/1987 | Van Heuvelen . |
| 4,731,726 | 3/1988 | Allen, III . |
| 4,734,360 | 3/1988 | Phillips . |
| 4,787,398 | 11/1988 | Garcia et al. . |
| 4,790,979 | 12/1988 | Terminiello et al. . |
| 4,805,623 | 2/1989 | Jobsis . |
| 4,824,639 | 4/1989 | Hildenbrand et al. . |
| 4,900,666 | 2/1990 | Phillips . |
| 4,927,516 | 5/1990 | Yamaguchi et al. . |
| 4,935,346 | 6/1990 | Phillips et al. . |
| 4,940,945 | 7/1990 | Littlejohn et al. . |
| 4,953,552 | 9/1990 | DeMarzo . |
| 4,994,167 | 2/1991 | Shults et al. . |
| 4,999,295 | 3/1991 | Asakura et al. . |
| 5,002,054 | 3/1991 | Ash et al. . |
| 5,019,974 | 5/1991 | Beckers . |
| 5,029,583 | 7/1991 | Meserolt et al. . |
| 5,049,487 | 9/1991 | Phillips et al. . |
| 5,053,199 | 10/1991 | Keiser et al. . |
| 5,054,499 | 10/1991 | Swierczek . |
| 5,059,394 | 10/1991 | Phillips et al. . |
| 5,066,859 | 11/1991 | Karkar et al. . |
| 5,147,606 | 9/1992 | Charlton et al. . |
| 5,179,005 | 1/1993 | Phillips et al. . |
| 5,182,707 | 1/1993 | Cooper et al. . |
| 5,187,100 | 2/1993 | Matzinger et al. . |
| 5,201,324 | 4/1993 | Swierczek . |
| 5,211,914 | 5/1993 | Vogel et al. . |
| 5,231,993 | 8/1993 | Haber et al. . |
| 5,272,060 | 12/1993 | Hamamoto et al. . |
| 5,279,294 | 1/1994 | Anderson et al. . |
| 5,304,468 | 4/1994 | Phillips et al. . |
| 5,306,623 | 4/1994 | Kiser et al. . |
| 5,307,263 | 4/1994 | Brown .................................. 364/413.09 |
| 5,366,609 | 11/1994 | White et al. ............................ 204/403 |
| 5,378,628 | 1/1995 | Gratzel et al. . |
| 5,402,798 | 4/1995 | Swierczek et al. . |
| 5,410,474 | 4/1995 | Fox . |
| 5,418,142 | 5/1995 | Kiser et al. . |
| 5,426,032 | 6/1995 | Phillips et al. . |
| 5,445,967 | 8/1995 | Deuter . |
| 5,451,350 | 9/1995 | Macho et al. . |
| 5,507,288 | 4/1996 | Bocker et al. . |
| 5,515,170 | 5/1996 | Matzinger et al. . |
| 5,522,255 | 6/1996 | Neel et al. . |
| 5,526,120 | 6/1996 | Jina et al. . |
| 5,547,702 | 8/1996 | Gleisner . |
| 5,556,761 | 9/1996 | Phillips . |
| 5,563,031 | 10/1996 | Yu . |
| 5,580,794 | 12/1996 | Allen . |
| 5,597,532 | 1/1997 | Connolly .................................. 422/58 |
| 5,620,863 | 4/1997 | Tomasco et al. . |
| 5,628,309 | 5/1997 | Brown . |
| 5,719,039 | 2/1998 | Kiser et al. . |

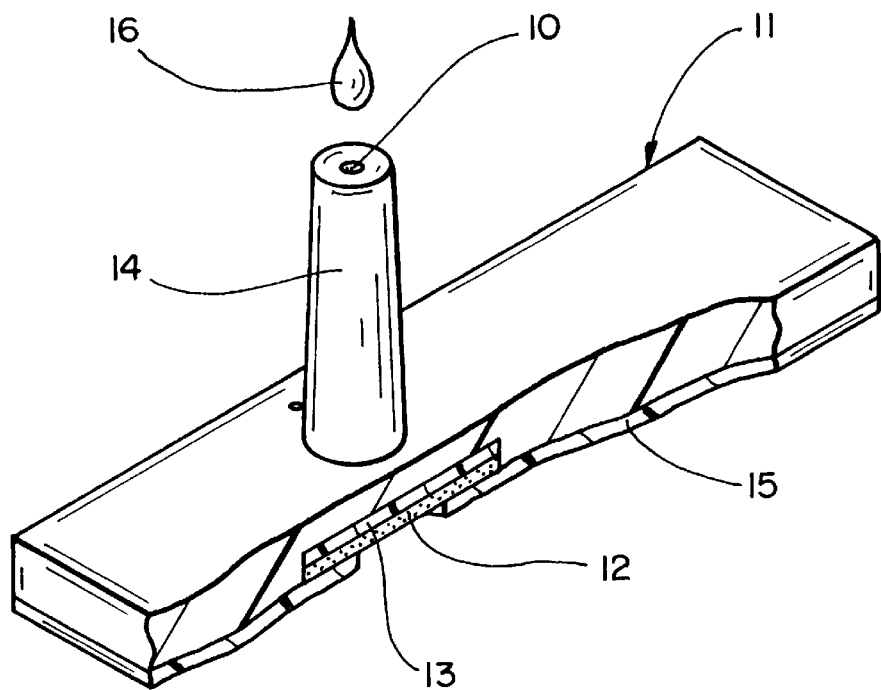
FIG_1A
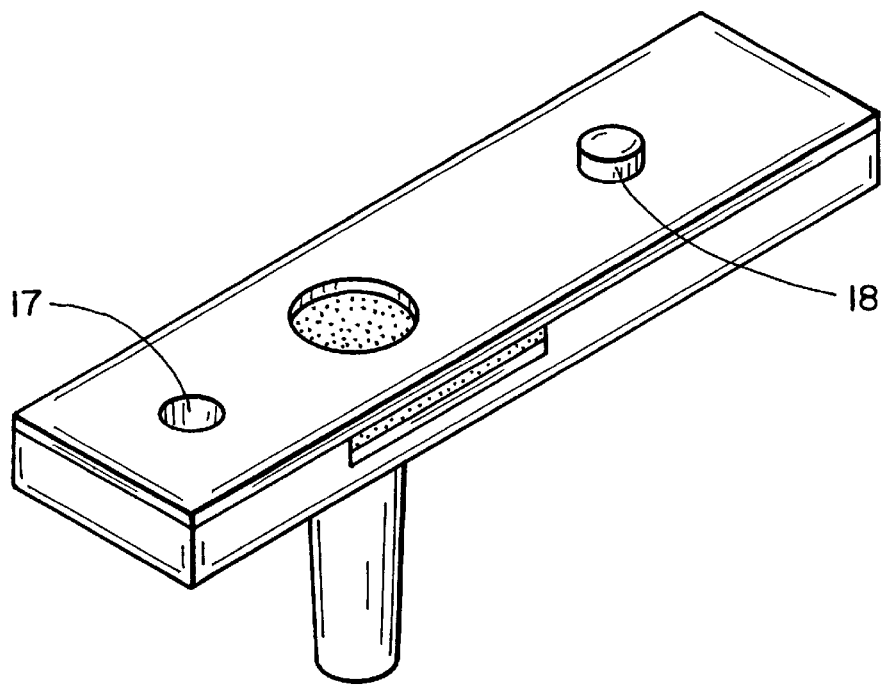
FIG_1B

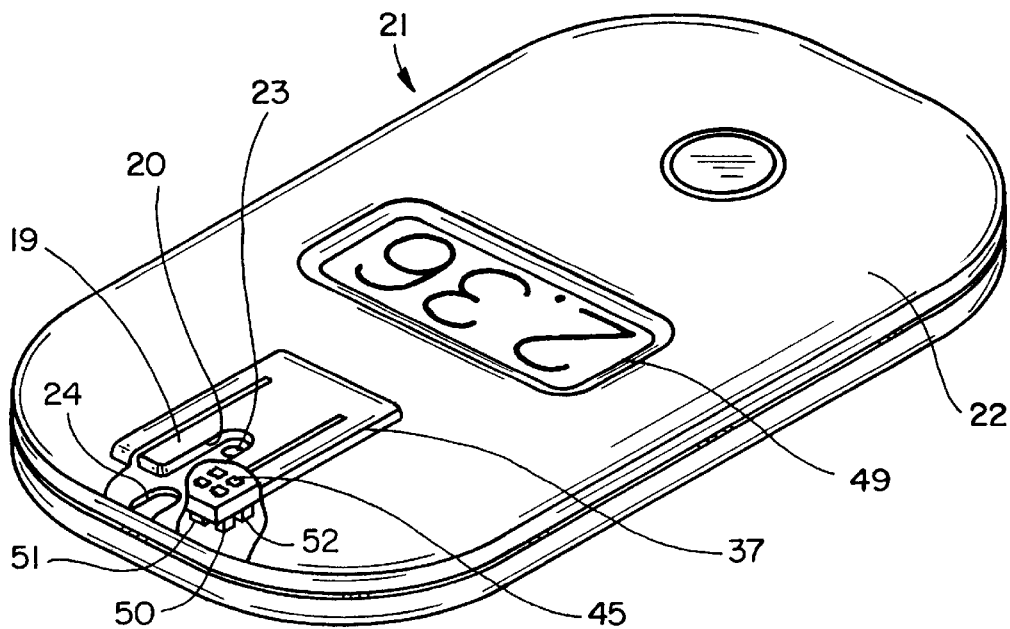
FIG_2
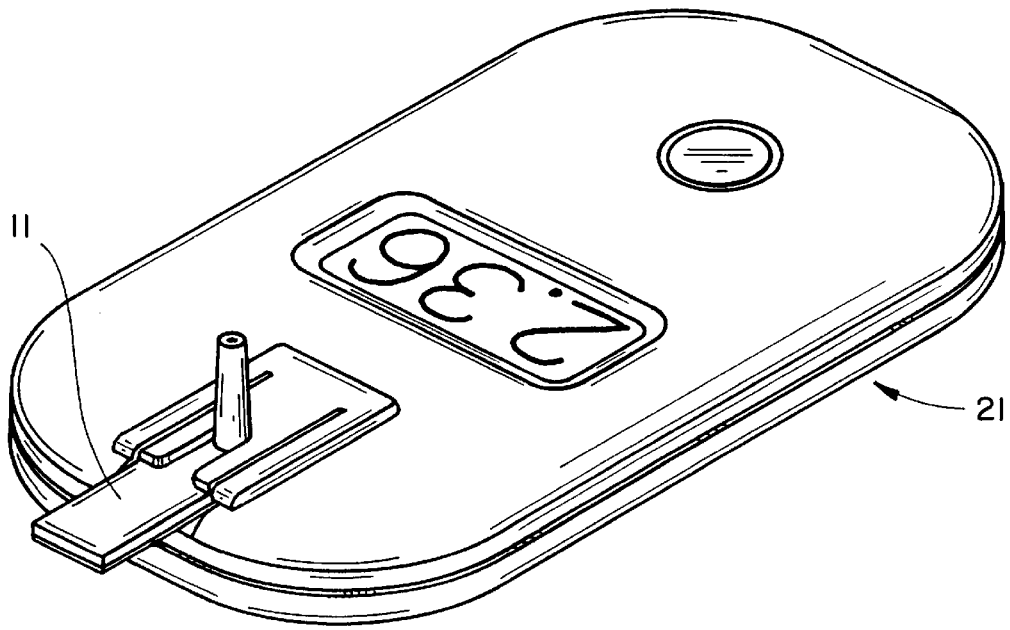
FIG_3

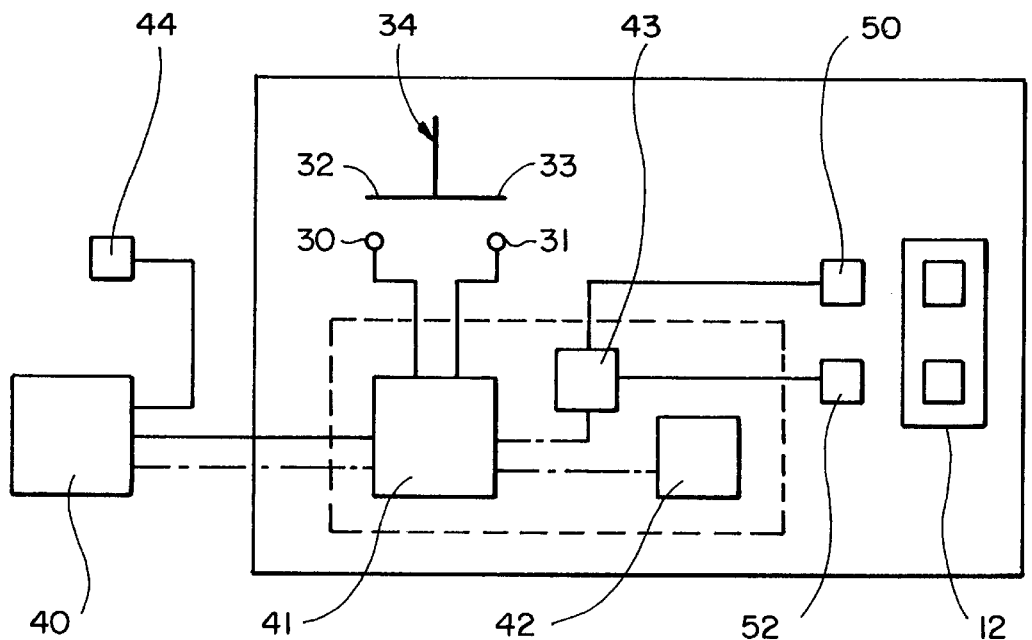
FIG_4
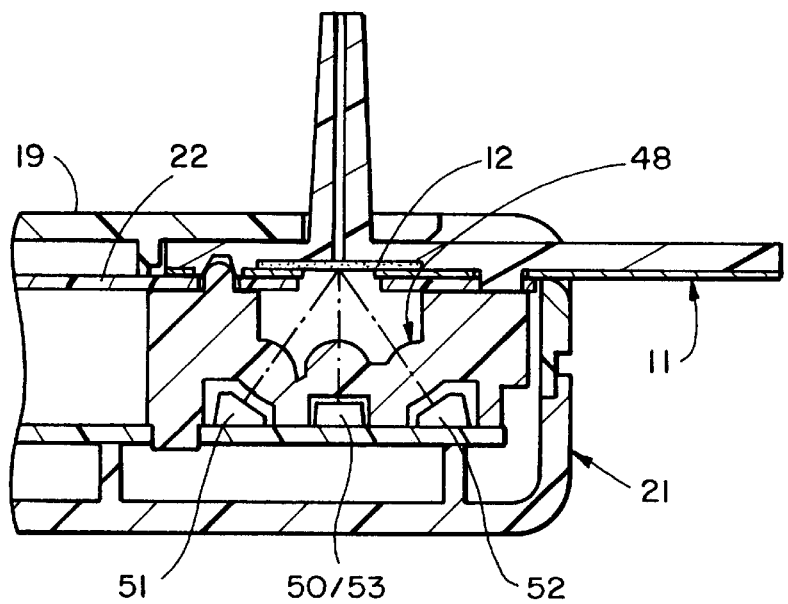
FIG_8

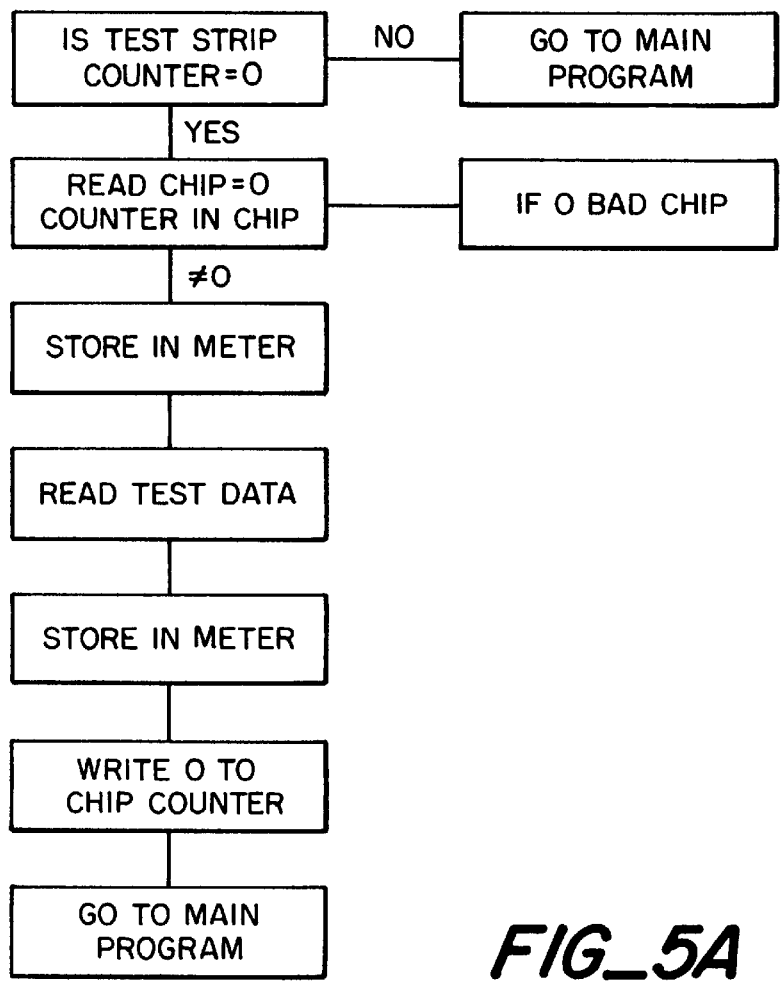
FIG_5A
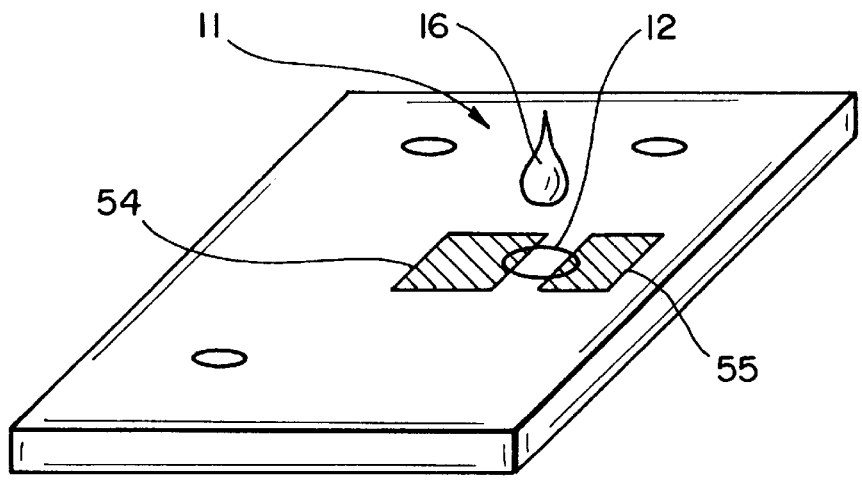
FIG_5B

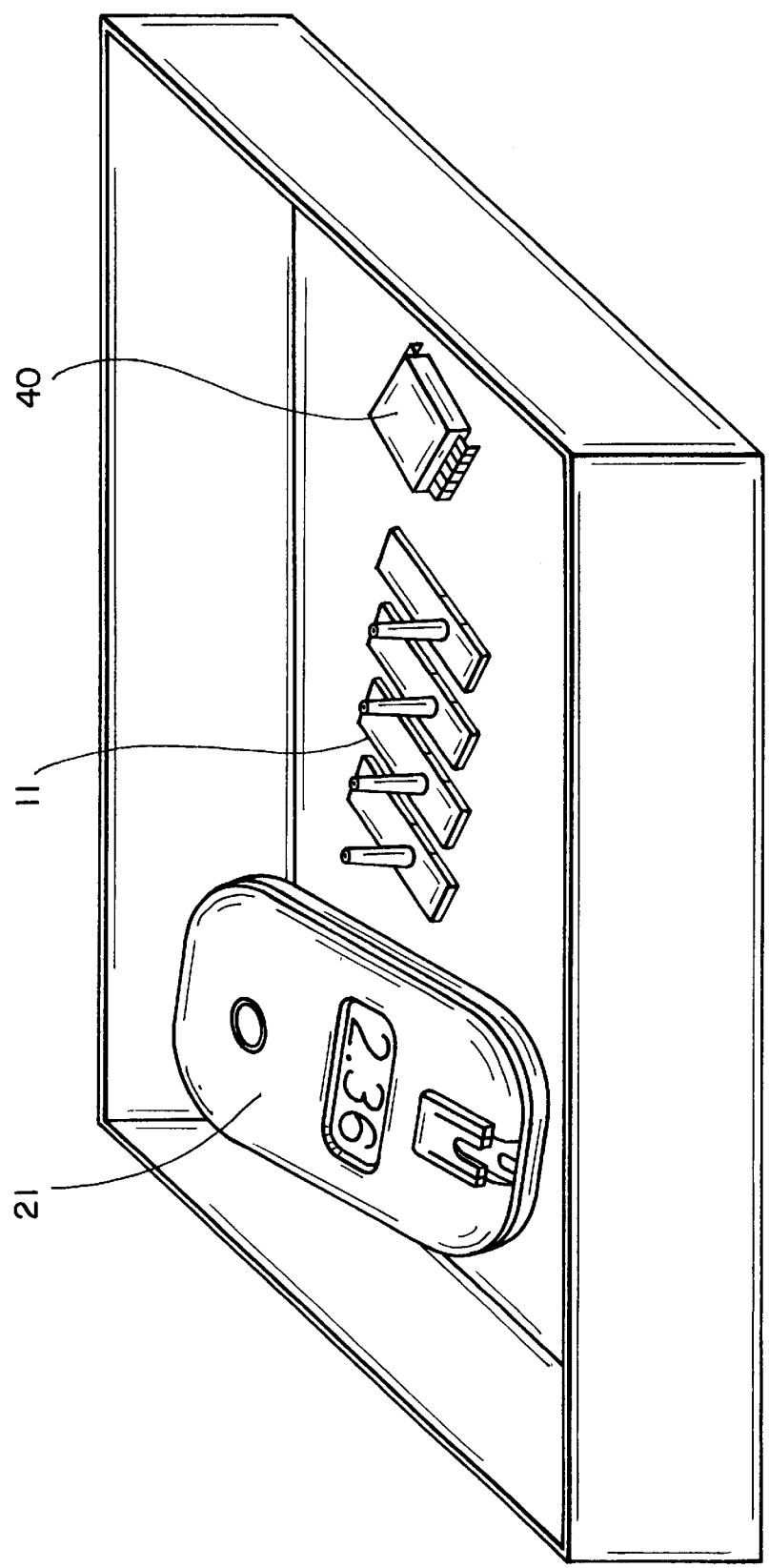
FIG_6

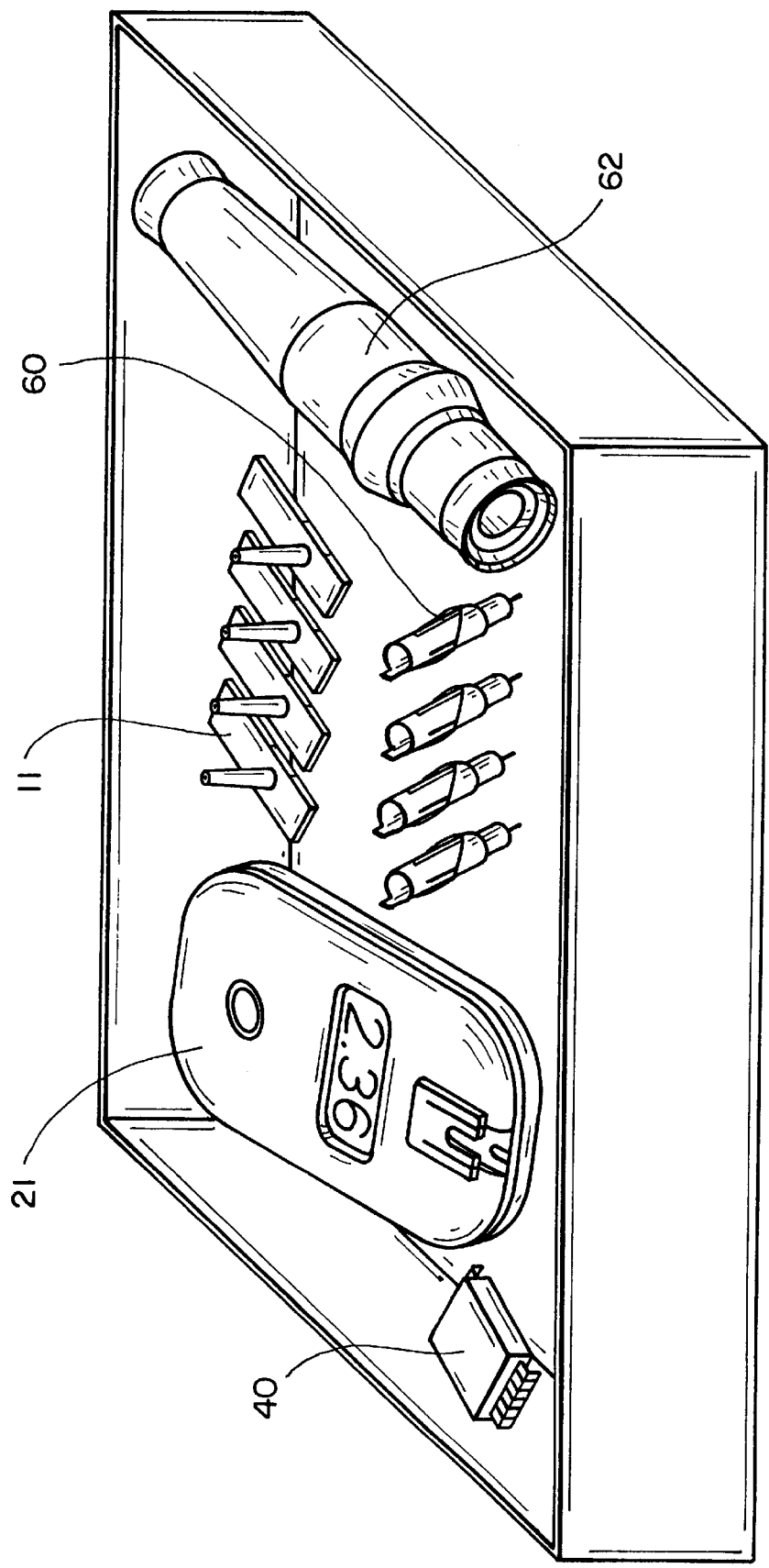
FIG_7

SYNCHRONIZED ANALYTE TESTING SYSTEM

This application claims benefit of Provisional No. 60/029,201, filed Oct. 30, 1996.

BACKGROUND OF THE INVENTION

1. Field of the Invention

The present invention relates to detection devices for determining the presence or concentration of analytes or biological agents in a sample, and more particularly, to systems using testing instruments to measure analyte activity on test strips impregnated with appropriate reagents.

2. Description of Related Art

The need for simple methods to determine the chemical and biological constituents in bodily fluids has increased as point of care testing has gained in popularity. A common application is the self monitoring of blood glucose concentrations by patients with diabetes. These patients frequently administer insulin or take other therapeutic actions based on the test results. As testing is generally recommended multiple times daily and may occur in any setting, an easy to use and relatively inexpensive method to accomplish this task is required. The costs of testing are significant to many diabetic patients, especially elderly patients with fixed incomes and those who are not reimbursed by health insurance plans.

In addition to chronic disease monitoring, there are other applications where simple, low cost testing at the point of care may be desired. For example, many practitioners believe that certain medications could be administered much more effectively, both from a medical outcomes and from a cost perspective, if the circulating level of such medications could be monitored during the course of treatment. Generally, if the level of an analyte or biological agent is important enough, the patient needs to go to a clinic or laboratory and submit to a venipuncture so a test may be run on an expensive clinical instrument. The ability to inexpensively monitor the patient either in the doctor's office or at home could lead to improved outcomes. Given the current pressures on improving the cost effectiveness of health care, inexpensive, easy to use alternatives to expensive test methods would be welcomed.

The National Institutes of Health conducted a large scale study to evaluate the benefit of long term tight control of the blood glucose for the diabetic patient. The study, known as the DCCT, proved that long term tight control of the blood glucose levels in patients had a direct relationship to the health of the patient. One way for the medical profession to monitor the control of a patient is for the patient to use a blood glucose monitoring system which has a memory unit to record the blood glucose level and other data such as date and time.

Many diabetics currently use a test method described in U.S. Pat. No. 5,304,468 to Phillips et al. This system is comprised of an electronic meter and a disposable reagent strip. The meter reads the color change of the strip which correlates to the concentration of the analyte in the sample applied to the strip. The meter is an expensive and complex instrument which uses multiple light sources or detectors to isolate the reagent color change from the sample color. The user must select the calibration code for the meter to match the calibration code of the test strips. In this way, the meter accommodates a wide range of test strip performance values.

U.S. Pat. No. 4,637,403 to Garcia et al. describes an integrated system which provides a method by which the patient lances the finger to get a sample of blood which is then used by the device to read the quantity of analyte in the sample. This system uses a complex reflectance system to read the analyte level in the sample.

U. S. Pat. No. 5,279,294 to Anderson et al. describes a hand held shirt pocket device for quantitative measurement of glucose or analytes in biological fluids. The device has a sophisticated electronics system and a sampling system integrated into one device to determine the quantity of analyte in a bodily fluid sample U.S. Pat. No. 5,515,170 to Matzinger et al. describes the difficulties of keeping a strip holder and optics system clean and the need to present the test strip in the proper perspective to the optics.

European Patent Specification 0 351 891 B1 Hill et al. describes an electrochemical system and electrodes which are suitable for the in vitro determination of blood glucose levels. The system requires the use of expensive electrodes and a sophisticated reader to determine blood glucose levels.

U.S. Pat. No. 4,994,167 to Shults et al. describes a measuring device for determining the presence and amount of a substance in a biological fluid using electrochemical methods. This system requires a complex instrument and method for the patient to determine the quantitative result.

U.S. Pat. No. 5,580,794 to Allen et al. describes a single use disposable measuring device for determining the presence and amount of a substance in a biological fluid using reflectance methods. This system utilizes an optics and electronics package which are mated in a single plane.

Single use disposable devices have been designed for the analysis of analytes in bodily fluids. U.S. Pat. No 3,298,789 to Mast describes a system in which whole blood is applied to a reagent strip. After a precise, user-timed interval, the blood must be wiped off by the user. An enzyme system reacts with the glucose present in the sample to create a color change which is proportional to the amount of glucose in the sample. The strip may be read visually, by comparing to a printed color intensity scale, or in an electronic instrument.

U.S. Pat. No. 5,418,142 to Kiser et al. describes a single use device which does not require blood removal or color matching. The amount of analyte present in the sample is read in a semiquantitative fashion.

U.S. Pat. No. 5,451,350 to Macho et al. describes a single use system for the determination of an analyte in a biological sample.

U.S. Pat. No. 5,522,255 to Neel et al. describes a fluid dose, flow and coagulation sensor for a medical instrument which uses a non-volatile electronic calibration device in the system to check the calibration of the reagent strip.

U.S. Pat. No. 5,053,199 to Keiser et. al. describes an electronically readable information carrier for use with a medical device.

U.S. Pat. No. 5,366,609 to White et. al. describes a biosensing meter with a pluggable memory key. This device uses a pluggable memory key which is used to control the operations of the meter.

U.S. Pat. No. 5,307,263 to Brown describes a modular microprocessor based health monitoring system designed to collect data from a health monitoring test system such as a blood glucose monitoring meter.

Although many improvements have been made, the cost and complexity of measuring analyte levels in biological samples remains a significant issue for patients and for the health care system. Even patients who are covered for blood glucose monitoring supplies must often purchase the meter and await reimbursement. The need to match the calibration of a meter and the strips or electrodes in use leads to errors in performance and adds cost and complexity for the manufacturers. The availability of a low cost, simplified quantitative test system for the periodic monitoring of constituents of biological fluids, such as glucose in blood, would make testing more accessible to patients and would improve their well-being and reduce the cost of their care.

Currently, existing calibration mechanisms require the loading of a calibration chip, calibration strip, inputting of a calibration code or use of a machine readable mechanism on the strip to modify the reaction interpretation of the meters. These methods can result in errors in reading of the analyte being tested for by using either the wrong calibration device with a lot of strips or entering the wrong calibration code for the lot of strips.

In addition, a system which requires a smaller fluid sample would be attractive to many patients. There has been a trend toward smaller sample sizes, but most devices still require about 10 $\mu L$ of blood. Many patients have difficulty routinely applying an adequate sample to the strips or electrodes. Inadequate sampling can cause erroneous results or may require that the user discard an expensive test strip and repeat the sample application procedure.

An additional issue is the use of out of date test strips with the meter. Currently the expiration date and expiration period after opening is printed on the container for the test strips. This presents a problem for the patient if he or she does not observe the dating information on the container. The strips can result in an error in the reading which can cause false response/treatment by the patient.

SUMMARY OF THE INVENTION

The invention overcomes the deficiencies of the prior art by providing a low cost testing instrument and single use test strips capable of reading small sample sizes, e.g. 3 $\mu L$, and determining the amount of an analyte in the small sample. The low cost nature of the testing instrument permits the packaging of the testing instrument and test strips together in a package, creating a synchronized system which may be used to perform a specific number of tests. The testing instrument is provided at no extra cost to the user, who benefits from having a fresh device with each new package of test strips purchased. This eliminates the need for the patient to make an investment in test equipment to monitor a specific condition or therapy.

In an alternate configuration, the device may be provided as part of a starter package including a sampling device and test strips. Replacement test strips could be purchased separately without the device or sampler if longer testing instrument life is preferable. For example, the desire to include additional features such as data management capabilities could add cost which would favor a longer useful life for the testing instrument.

The testing instrument incorporates a molded lens optic system consisting of one or more channels and a simple electronics package consisting of light emitting diodes (LEDs), analog to digital conversion electronics, a processor unit, Read Only Memory and a digital display system. The testing instrument case has a positioning system which interfaces with the test strip to create positive location and alignment for the reagent test pad within the strip and the optics.

The applied bodily fluid reacts with the reagents impregnated in the test pad within the test strip and the resulting color change is read by the optics system. The signal is converted and displayed on the digital readout as the concentration of the analyte in the sample.

An advantageous feature in accordance with the invention is the use of a small sample sizes, e.g., about 3 $\mu L$, which is a fraction of the volume required for most blood glucose tests and could be more readily obtained by patients.

Another advantageous feature in accordance with the invention is the provision of a simple low cost testing instrument and a complimentary reagent test strip.

Another advantageous feature in accordance to the invention is the use of reagent test strips that are calibrated to the testing instrument and/or an intelligent calibration device which may each be one-time readable mechanisms, eliminating the potential problems of re-use of the calibration device with the wrong set of test strips.

Another advantageous feature in accordance with the invention is a testing instrument which is precalibrated or synchronized to the lot of reagents test strips with which it is supplied, eliminating the need for the user to match or enter calibration information.

Another advantageous feature in accordance with the invention is a system which is designed for a predetermined number of test results, minimizing upkeep such as cleaning or battery replacement.

Another advantageous feature in accordance with the invention is the elimination of the need for a separate test strip holder, simplifying the interface of the disposable portion of the test system with the re-usable testing instrument.

Another advantageous feature in accordance with the invention is the elimination of the need for a patient to calibrate the meter for the test strips or keep track of expiration dating by placing the information on a single use calibration chip.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 1 is a perspective view of one embodiment of a test strip comprised of a test pad and holder for body fluid analysis.

FIG. 2 is a perspective view of one embodiment of the testing instrument having a test pad holder.

FIG. 3 illustrates the testing instrument and a test strip in communication with the test strip.

FIG. 4 is a block diagram of the testing instrument electronics and optics for reading the test strip.

FIGS. 5A and 5B illustrate a method of confirming the wetting of the test pad and contact to start the timing of the testing instrument.

FIG. 6 shows a kit of the system including testing instrument and test strips.

FIG. 7 shows a kit of the system including testing instrument, test strips and sampling devices.

FIG. 8 shows the use of two detectors and two emitters in an optics system.

DESCRIPTION OF THE PREFERRED EMBODIMENTS

FIG. 1 is a perspective view showing the test strip 11 for use with the detection device in accordance with the invention, the test strip 11 comprising a test pad 12 and holder 13 for analysis of bodily fluid 16. The test strip 11 provides a handle 14 for the patient to hold the strip 11. The handle operates as a wick to transfer the bodily fluid 16 to the test pad 12 and is provided with a channel 10 for this purpose. The test pad 12 may be formed from bibulous matrix which has been impregnated with a reagent system comprised of enzymes, indicators and blood separation agents.

Test strip 11 is provided with an alignment mechanism which may comprise recess 17 and projection 18 disposed on bottom portion 15 of the test strip 11. These operate to insure positive location and orientation of the test strip 11 with respect to the testing instrument 21 of the invention by engaging corresponding portions of the testing instrument as explained below. Of course it is contemplated that other test strip configurations can be used with the system of the invention without patentable departure from the spirit and scope of the invention.

FIG. 2 is a perspective view of testing instrument 21 which is used to read test strip 11 in accordance with the invention. The testing instrument 21 has a housing 22 which is provided with optics view window 23 and a docking portion 37 for mating with alignment recess 17 and projection 18 of test strip 11. Docking portion 37 may comprise a slot 20 disposed in a retaining clip 19 which operates to guide handle 14 of test strip 11 into position, along with a recess 24 to mate with projection 18 of the test strip 11. Proper alignment for accurate reading is thereby insured, as illustrated in FIG. 3, which shows the testing instrument 21 in operational position in communication with the test strip 11.

Testing instrument 21 is also provided with a sensor 45 for measuring the analyte concentration in sample 16, along with a display 49 for displaying the result. The sensor 45 may be optical in nature, and as shown in FIG. 8, may comprise paired light emitter and detector devices. Specifically, an LED emitter 50 and A photodetector 51 measure reflected light from the sample-containing test pad 12. This reflected light is proportional to the amount of analyte in the sample as manifested by the extent of reaction of the sample/analyte with the reagent on the test pad 12. Ambient light is blocked by a design of test strip 11 and testing instrument 21 which minimizes error induced by ambient light corrupting the reflectance reading. Such a design may include appropriately limiting the size of view window 23 while selecting sufficiently opaque materials to form the material of the housing 22 from which view window 23 is formed, thus operating to effectively form an optical shield. Insuring proper alignment in accordance with the invention also serves to minimize ambient light corruption.

In accordance with the invention, numerous optical schemes may be employed, including use of transmitted rather than reflected light, multiple LED/detector pairs and various arrangements thereof. It is also contemplated that various light source:light detector ratios maybe used, departing from the one-to-one correspondence disclosed.

In accordance with the invention, an LED 53 is also provided and corresponds with a photodetector 52. The photodetectors 51 and 52 may be selected to operate at different light intensity levels, such that light below or at a predetermined intensity threshold is measured by one photodetector, while light above the threshold is measured by the other photodetector. Alternatively, one detector can be used to measure reflectance of a particular color component, while the other measures the reflectance of a different color component, or one detector can measure overall light intensity while the other measures a color component. Also, a reference detector (not shown) could be employed to compensate for the deterioration of the LED intensity over time. In alternative arrangement, the measurement from one detector can be used to provide a compensation for hematocrit level or oxygen content of the blood. One of ordinary skill in the art will realize many modifications and remain within the purview of the invention.

An optical arrangement in accordance with the invention is further provided with a molded plastic lens system 48 to focus light to and from the sample on the test pad 12. Such an arrangement provides the capability of focusing the light to and from a small reaction area, which reduces the size of the test pad 12 and the amount of sample required to effect the testing procedure. Advantages thus realized include reduction in size/cost of the matrix employed and quantity of expensive reagents required.

The optics of the invention may include appropriate optical filtering to optimize measurement, or electronic filtering and masking techniques may be employed to improve signal-to-noise levels. An optical filtering scheme of the invention, when blood analysis is to be performed, involves the use of existing membrane materials with a blocking filler to create an opaque membrane which blocks interference from red blood cells and can assist in the separation of red blood cells from relatively clear fluid.

Another optical configuration uses multiple LED and photodetector pairs. A first pair is used to achieve the primary analyte determination. A second pair is used to monitor test initiation and to quantify hemoglobin and hematocrit. Subsequent pairs are used to monitor native color effects of lympic and icteric samples. Additional optical pairs are used in association with added chemical components in the strip for specific determination of possible interference factors such as pH, specific gravity, etc. as well as for specific determination of additional analytes such as cholesterol, triglycerides, etc. Such analysis, possibly using different wavelengths, provides significant benefits to overcoming interfering effects from the sample and the environment. By selecting wavelength pairs which are tuned to detect components of the test, it is possible to isolate and quantify the analyte, hematocrit and red blood cell contributions in a testing event. In accordance with the invention, interference from the environment is minimized by separating its effects and monitoring each one independently using multiple optical systems. Through detection and quantification, the individual contribution to the measurement can be subtracted from the analyte measurement. With the ever decreasing cost of computing power, and a unique of constructing multiple optical systems at very low cost, the approach of the invention is readily applicable to home diagnostic use.

The test strip 11 is comprised of a test pad 12 situated in a test pad holder 13. This holder provides a means for accurately positioning the test pad 12 with respect to the sensor 45 in addition to providing a means for blocking ambient light from effecting the analysis. The test pad 12 is impregnated with the appropriate chemistry to permit a colormetric analysis of the analyte being tested and may therefore provide a stable absorbent substrate.

The test strip 11 of this invention differs from current test strips in multiple ways. For current test strips, the nonporous support provides a handle for the patient [U.S. Pat. No. 5,526,120 Jina et al.], and/or a means of aligning the test strip in a strip holder [U.S. Pat. No. 5,515,170 Matzinger et al.] The test strip of this invention does provide a support for the test pad. The strip positively seats on the testing instrument, assuring proper alignment. It also seals the optics area from ambient light and blood contamination. Thus it provides all of the functionality of a test strip and test strip holder of a conventional reflectance system. The test strip provides additional benefits in being removed after each test, facilitating easy access to the optics area for cleaning if required. With this combination part, the overall cost of the system is further reduced. When inserted into the detection device 21, the test strip 11 contacts complete a circuit which turns the device on. The device is turned off upon removal of the test strip. This eliminates a need for a separate on/off circuit or patient action to turn the testing instrument on or off.

The signal producing system impregnated in the test pad matrix can be formed from different indicator systems such as 3-methyl-2-benzothiazolinone hydrazone (MBTH) and 8-anilino-1-naphthalenessulfonate(ANS) [U.S. Pat. No.5, 453,360 Yu], MBTH and 3-dimethylaminobenzoic acid (DMAB) [U.S. Pat. No. 5,049,487 Phillips et al.], 3-methyl-2-benzothiazolinone-hydrazone-sulfonate sodium salt (MBTH-$SO_4$) and ANS [U.S. patent application Ser. No. 08/628,794 Douglas et al.], MBTH-$SO_4$ and N-(3-sulfopropyl)aniline (HALPS) [U.S. Pat. No. 4,396,714 Maeda et al. and U.S. patent application Ser. No. 08/628,794 Douglas et al.], MBTH-$SO_4$ and N- Ethyl-N-(3-sulfopropyl) aniline ALPS [U.S. Pat. No. 4,396,714 Maeda et. al. and U.S. patent application Ser. No. 08/628,794 Douglas et al.]. One skilled in the art could devise an alternate indicator system. The oxidase enzyme system contained in the reagent pad produces hydrogen peroxide which is used to convert the indicator with the assistance of peroxidase which acts as the catalyst.

In the most preferred embodiment the reagents are impregnated into a porous membrane by submerging the dry membrane into a reagent dip. Excess fluid is wiped from the membrane surface and the membrane is gently dried in an oven. At this point, subsequent dipping and drying can be conducted. A preferred embodiment for a two dip process is:

| MBTH-$SO_4$ & ALPS Formulation | |
|---|---|
| | Final Concentrations |
| A Dip | |
| In Citrate Buffer, pH 7 stock A Dip | 0.1 M |
| EDTA | 0.08% |
| mannitol | 0.19% |
| Gantrez-S95 | 0.53% |
| Klucel 99-EF | 20 uM |
| Crotein-SPA | 7.45% |
| enzyme reagents | |
| Glucose Oxidase | 0.92% |
| Peroxidase | 0.54% |
| B Dip | |
| In 70% Ethanol | |
| MBTH-$SO_4$ | 0.66% |
| ALPS | 2.00% |
| SOS | 0.20% |

The assembly of a system kit comprised of a testing instrument and a specific number of synchronized test strips for the testing of a specific analyte can provide a simple, cost effective test method and procedure.

FIG. 4 is a block diagram showing the processing operation of the invention. Testing instrument 21 comprises a microprocessor 41 which controls the operation of the testing instrument 21. The testing instrument 21 is activated by a switching mechanism which may comprise a mechanical ON button 34 and contacts 30–33 which close an appropriate circuit when the button 34 is depressed. Closing of this circuit triggers operation of the device by notifying the microprocessor 41 that a measurement reading of a positioned test strip 11 is to be performed. The test strip may be one of a number of test strips in the set, and a counter keeps track of these. Alternatively, the circuit may be closed via a fluid connection using the test sample, with the contacts 30 and 31 operating as probes provided for making contact with the test pad 12 of the test strip 11 to thereby activate the testing instrument 21 upon detection of the sample on the appropriately positioned test strip 11.

FIGS. 5A and 5B illustrate a method of confirming the wetting of the test pad 12 to start the testing instrument 21. The test strip 11 of FIG. 5B is configured to have contacts 54 and 55 disposed on the test pad 12 thereof. The contacts 54 and 55 are spaced apart a finite distance, and are only in electrical communication by virtue of a fluid contact formed by the sample. The sample 16 is applied to the test strip 11, wetting the test pad 12 and contacts 54 and 55. The contacts 54 and 55 are in communication with contacts 30 and 31 on testing instrument 21 so when wetted this completes a circuit which starts the testing instrument 21 and begins the analysis of the sample. Of course, other activation schemes can be utilized by the invention. Two such schemes may be optical or mechanical detection of the test strip 11 in docking portion 37.

Following activation, measurement of the reaction of the sample with the reagent on the test strip 11 is effected using the optical sensor 45. Of course, the sensor itself need not be of the optical type—other expedients, such as electrochemical detection, e.g., fall within the purview of the invention. The microprocessor derives an electrical signal from the sensor 45, comprising electro-optical devices 50 and 52, and processes it to generate a detection signal indicative of analyte concentration in the tested sample. An ASIC 43 (application-specific integrated circuit) and a memory, such as RAM (random access memory) 42 or a ROM (read only memory) may be used in conjunction with the microprocessor 41, while the results of the measurement may then be displayed using LCD display 49. The results may alternatively be stored in RAM 42 for subsequent viewing or processing. The subsequent processing may be performed using the measuring instrument 21 itself, or using other devices to which the measurement results can be downloaded. One possibility in accordance with the invention is a modem link with a remote processing unit, using, e.g., telephone lines. The information may also be downloaded for storage at an internet location or electronic bulletin board for subsequent retrieval and processing or review by medical professionals.

One feature in accordance with the invention is the use of a calibration chip 40 as shown in FIG. 4. The calibration chip is detachably connectable to the testing instrument 21 for electronic communication with the microprocessor 41. It may be any form of volatile or non-volatile memory including single use microprocessors, EPROMs or EEPROMs thus forming an intelligent chip permitting intelligent data transfer between the chip and the testing instrument 21. Calibration chip 40 contains calibration information which is uniquely specific to the reagent provided with a particular set of test strips 11 distributed with the calibration chip. In this way, lot differences in the reagent can be compensated for using the required information and sophistication, while at the same time obviating the need for the user to enter or contribute to this information. This minimizes error and greatly facilitates use and accuracy of the testing instrument 21 of the invention.

The color formed after applying the bodily fluid to the reagent test pad is proportional to the amount of analyte in the applied sample 16. The testing instrument 21, via sensor 45 and microprocessor 41, measures the change in reflectance due to the development of the specific color generated by the reagent on the test strip 11. This is either used as the input to a function which relates reflectance to analyte level or to a table which correlates reflectance value to analyte level. The function or the table must be stored within the system for it to produce and display, on display 49, a reading of the analyte level in the sample 16. While most meters in use today employ functions to convert reflectance readings to analyte concentration, this approach requires that the function be stable and well understood. The use of a look up table permits the storage of specific values for reflectance and their corresponding analyte levels. The testing instrument uses this table and interpolates between the table values to give relatively accurate readings. This is achievable in a system such as that described by this invention as the table can quickly be generated for each reagent lot produced.

In the preferred embodiment, calibration is based on the response produced by a specific lot of test strips. In this manner, there is no need to presort and test the LEDs 50 and 53, significantly reducing the cost of the sensor 45. In addition, this calibration step during manufacture allows the device to compensate for a wide area of variables normally found in reflectance systems. The specific calibration data for the test strips 11 shipped with the testing instrument can be stored in the unit's read only memory (not shown). Alternatively, a master strip can be provided for setting the calibration information for that lot of strips and the master strip can be distributed therewith. A counter may be provided to limit the testing instrument 21 to performing only a specific number of tests which correlates to the quantity of test strips 11 shipped with the device. Other limitations can be built-in, such as expiration date information pertaining to the specific lot of test strips 11, with this information being contained in the measuring instrument's ROM or in the calibration chip 40 or in the master strip.

A more traditional approach to calibration may alternatively be taken. A calibration algorithm, with several settings if necessary, could be programmed into the system if the testing instrument has a longer projected life and is to be used with multiple sets of test strips.

If a microprocessor is used for the calibration chip, the chip may be provided with its own power source for memory information retention. To prevent re-use when an EPROM or other memory device is used as the calibration chip, an optional mechanical latch 44 which would eliminate the ability to engage the calibration chip into the testing instrument 21 a second time. Similarly, when a microprocessor or EEPROM or other memory device is used, the calibration chip 40 may have its data overwritten or an indicator bit thereof be written by the microprocessor 41 following its use to prevent reuse. The calibration information stored in the calibration chip 40 is thus downloaded to the processor memory 42, and the calibration chip is disabled, preventing reuse thereof. The calibration information contains the permitted number of test strip analyses to be performed, the number corresponding to the number of test strips provided with the kit. The calibration chip itself can then be disposed of.

Alternatively, a counter (not shown) may be provided in the calibration chip, the counter being decremented each time the chip is read. In this manner, only a limited number of readings, corresponding to the number of test strips 11 provided with the calibration chip 40, can be performed. It is also contemplated that calibration information provides and expiration date preventing use of the calibration chip and/or associated strips thereafter, or a duration can be measured after which use of the chip and/or associated strips is precluded. The duration can be commenced from time of opening a package in which the kit is provided, or from any other similar time, such as the time of first use of the calibration chip 40. The ordinarily skilled artisan will find numerous variations can be effected without departure from the spirit and scope of the invention.

The patient uses the system by removing the testing instrument from the packaging and placing it on a firm surface. The next step is to remove a test strip and insert it in the testing instrument. Inserting the test strip activates the unit, eliminating the need for a power on/off button or switch. The patient then uses either a sampler 60 (FIG. 7) from the kit or one procured separately to draw a sample of capillary blood. The kit may optionally be provided with a sampling device 62 as well. The sample is applied to the test strip, initiating a timing sequence, and the testing instrument displays the results after an appropriate time. Alternatively, the patient may first apply the blood sample to the test strip, then insert the strip into the testing instrument to activate the test cycle and read out of test results.

The subject invention provides improvements over existing technology in use today in several ways. The preferred embodiment of the invention eliminates the need for a patient to purchase a costly system to conduct routine testing of body fluids. It also eliminates the existing dependence on the customer to maintain the testing instrument and monitor/compensate for reagent lot differences. The invention provides this easy to use format for analytes such as glucose by incorporating advanced lens based optics and low cost modern electronics. The use of lens based optics permits the system to focus on small reaction area which reduces the size of the test pad. The resulting small test pad reduces the cost of the matrix employed and the quantity of expensive reagents needed to conduct an accurate assay using an oxidase and peroxidase chemistry. With a smaller test pad, a smaller sample volume is adequate. The system conserves the energy used and minimizes the amount of light required by the system to determine the color change. The optics modules are calibrated during the manufacture of the testing instrument.

An important feature in accordance with the invention is the manufacture and calibration of the testing instrument 21 for use with a specific quantity of test strips 11 which have been matched at the factory. This limits the need for calibration codes, and minimizes the maintenance required by the patient in the form of cleaning, battery replacement and calibration code changes. It also improves the system's ability to provide long term accurate results because a testing instrument is synchronized with only certain test strips. Once they have been used, a complete new kit is acquired with a testing instrument calibrated specifically for those test strips. This eliminates much of the compromise in system performance found in current products which have to work with strips made over a wide range of production conditions and input states.

The above are exemplary modes of carrying out the invention and are not intended to be limiting. It will be apparent to those skilled in the art that modifications thereto can be made without departure from the spirit and scope of the invention as set forth by the following claims.

What is claimed is:

1. A synchronized detection device for detecting the presence of an analyte in a sample based on a physically detectable reaction of the sample with a reagent the device comprising:

a set of test strips each containing the reagent disposed thereon, each set containing at least one test strip;

calibration means corresponding to the set of test strips and containing calibration information uniquely characteristic to the reagent in the set of test strips;

a housing having a docking portion for engaging at least one of the test strips;

a sensor disposed at least partially in the housing an adapted to generate an electrical signal responsive to the reaction of the sample with the reagent;

a processor disposed at least partially in the housing an adapted to operate in accordance with the calibration means to generate a detection signal representative of the presence of the analyte in the sample;

the detection device is adapted for use a predetermined number of times, the processor tabulating the predetermined number of times using information contained in the calibration means; and the processor disabling use of the detection device after the predetermined number of times.

2. The device of claim 1, wherein the detection device is adapted for use a predtermined number of times corresponding to the number of test strips in the set.

3. The device of claim 1, wherein the processor is adapted to disable use of the detection device after a predetermined date.

4. The device of claim 1, wherein the calibration means comprises a chip containing correlation information for correlating the electrical signal to the detection signal.

5. The device of claim 4, wherein the detection device is adapted for use a plurality of said chips, each chip corresponding to an associated set of test strips and adapted to detachably connect to the housing.

6. The device of claim 4, wherein the correlation information is based on a predetermined mathematical function.

7. The device of claim 4, wherein the correlation information is based on a lookup table.

8. The device of claim 5, wherein each chip is adapted for use a predetermined number of times corresponding to the number of test strips in an associated set, the predetermined number of times being tabulated by the processor, the processor disabling use of the chip after the predetermined number of times.

9. The device claim 5, wherein each chip is adapted for use up to a predetermined date, the processor disabling the use of the chip after the predetermined date.

10. The device of claim 1, wherein the calibration means devices correlation information from a master test strip contained in the set.

11. The device of claim 1, wherein the docking portion is adapted to positively locate the test strip in a predtermined orientation relative to the sensor.

12. The device of claim 11, wherein the docking portion is adapted to matingly engage the test strip using engagment pins and corresponding holes such that only a successful mating achieves the predetermined orientation.

13. The device of claim 1, wherein the sensor comprises at least one LED and associated photodetector.

14. The device of claim 13, wherein the sensor comprises a first LED adapted to operate below a threshold radiation intensity and a second LED adapted to operate above the threshold radiation intensity.

15. The device of claim 13, wherein the sensor comprises a first LED adapted to detect total reflectance from the reaction and a second LED adapted to measure reflectance of a predetermined color component of the reaction.

16. The device of claim 13, wherein the sensor is provided with at least one molded lens optic system for focusing light.

17. The device of claim 1, further comprising a memory for storing the detection signal.

18. The device of claim 17, further comprising a modem for downloading the detection signal from the memory to a location remote from the detection device.

19. The device of claim 18, wherein the modem is disposed in a communication module which detachably engages the detection device for communication therewith, and which communicates with a storage device located at the remote location.

20. The device of claim 1, wherein the detection device is activated by an electromechanical switch triggered by the presence of a test strip in the docking portion.

21. The device of claim 1, wherein the detection device is activated by an optical switch triggered by the presence of a test strip in the docking portion.

22. The device of claim 1, wherein the detection device is activated by a pair of electrodes which sense the presence of the sample on a test strip disposed in the docking portion.

23. The device of claim 1, wherein the sensor comprises a pair of electrodes in electrical communication with sample.

24. The device of claim 13, wherein the photodetector is shielded from ambient radiation.

25. The device of claim 1, wherein a set of samplers is provided with the detection device, the number of samplers corresponding to the number test strips.

26. The device of claim 1, wherein the detection signal is displayed on a displayed disposed on the housing.

27. The device of the claim 26, wherein the display is an LCD device.

28. The device of claim 4, further comprising a memory, the correlation information being uploaded from the chip and stored in the memory.

29. The device of claim 28, wherein the chip is disabled following uploading.

30. The device of claim 28, further comprising a mechanical latch preventing multiple uploadings.

31. The device of claim 4, wherein the chip is provided with a counter, the correlation information being read by the processor a predetermined number of times corresponding to the number of test strips in an associated set of test strips, the counter being decremented with each reading.

32. The device of claim 1, wherein the processor prevents use of the calibration means following a predetermined duration.

33. The device of claim 1, wherein a sampling device is provided with the detection device.

34. The device of claim 25, wherein a sampling device is provided with the detection device.

35. The device of claim 4, wherein the chip is read once and disabled, the calibration information being stored for a specific number of tests corresponding to the number of test strips in associated set of test strips.

36. The device of claim 4, wherein the chip comprises an EEPROM.

37. The device of claim 4, wherein the chip comprises a microprocessor adapted to permit intelligent data transfer.

38. The device of claim 4, wherein the chip comprises an EPROM.

39. The device of claim 1, wherein the calibration means comprises a ROM contained within the housing of the device.

* * * * *